(12) United States Patent
Rains, Jr. et al.

(10) Patent No.: US 9,662,409 B2
(45) Date of Patent: May 30, 2017

(54) COMBINATORIAL LIGHT DEVICE FOR GENERAL LIGHTING AND LIGHTING WITH BENEFICIAL WAVELENGTHS

(71) Applicant: ABL IP HOLDING LLC, Conyers, GA (US)

(72) Inventors: Jack C. Rains, Jr., Herndon, VA (US); David P. Ramer, Reston, VA (US); Januk Aggarwal, Tysons Corner, VA (US)

(73) Assignee: ABL IP Holding LLC, Conyers, GA (US)

( * ) Notice: Subject to any disclaimer, the term of this patent is extended or adjusted under 35 U.S.C. 154(b) by 367 days.

(21) Appl. No.: 14/286,065

(22) Filed: May 23, 2014

(65) Prior Publication Data

US 2015/0335246 A1 Nov. 26, 2015

(51) Int. Cl.
*F21V 9/00* (2015.01)
*A61L 2/10* (2006.01)
(Continued)

(52) U.S. Cl.
CPC ........ *A61L 2/10* (2013.01); *F21V 9/16* (2013.01); *F21V 14/003* (2013.01); *F21V 23/003* (2013.01); *A61N 5/0619* (2013.01); *A61N 2005/0652* (2013.01); *A61N 2005/0659* (2013.01); *A61N 2005/0661* (2013.01); *F21Y 2101/00* (2013.01); *F21Y 2105/10* (2016.08);
(Continued)

(58) Field of Classification Search
CPC ........ A61L 2/10; F21V 23/003; F21V 14/003; F21V 9/16; A61N 5/0619; A61N 2005/0659; A61N 2005/0652; A61N 2005/0661; F21Y 2105/003; F21Y 2113/005

See application file for complete search history.

(56) References Cited

U.S. PATENT DOCUMENTS

| 4,091,441 A | * | 5/1978 | Ott | .................. A61N 5/0618 315/153 |
| 5,877,490 A | | 3/1999 | Ramer et al. | |

(Continued)

OTHER PUBLICATIONS

Photonics.com, "207-nm UV Light May Reduce Surgical Infections", Oct. 17, 2013, http://www.photonics.com/Article.aspx?AID=55109.

(Continued)

*Primary Examiner* — Y M. Lee
(74) *Attorney, Agent, or Firm* — RatnerPrestia (57) ABSTRACT

A lighting device includes a first light source configured to generate light for illumination of a space and a second light source configured to generate light of a particular wavelength independently from the first light source. The light generated by the second light source is output at a sufficient intensity so as to reasonably expect to support an intended benefit other than illumination of the space. The first light source and the second light source are integrated into the same lighting device. The lighting device includes an optical element coupled to the first and second light sources that is configured to produce a light output of the lighting device. The lighting device outputs the light for illumination of the space and the light of the particular wavelength for the other intended benefit from the second light source via the same output of the lighting device.

20 Claims, 5 Drawing Sheets

(51) Int. Cl.

| | |
|---|---|
| *F21V 23/00* | (2015.01) |
| *F21V 14/00* | (2006.01) |
| *F21V 9/16* | (2006.01) |
| *A61N 5/06* | (2006.01) |
| *F21Y 101/00* | (2016.01) |
| *F21Y 105/12* | (2016.01) |
| *F21Y 105/10* | (2016.01) |
| *F21Y 115/10* | (2016.01) |
| *F21Y 113/13* | (2016.01) |

(52) U.S. Cl.
CPC ....... *F21Y 2105/12* (2016.08); *F21Y 2113/13* (2016.08); *F21Y 2115/10* (2016.08)

(56) References Cited

U.S. PATENT DOCUMENTS

| | | | |
|---|---|---|---|
| 5,914,487 | A | 6/1999 | Ramer et al. |
| 6,995,355 | B2 | 2/2006 | Rains et al. |
| 8,021,008 | B2 | 9/2011 | Ramer |
| 8,172,424 | B2 | 5/2012 | Phipps et al. |
| 8,205,998 | B2 | 6/2012 | Ramer et al. |
| 8,282,241 | B2 | 10/2012 | Ramer et al. |
| 8,330,373 | B2 | 12/2012 | Ramer et al. |
| 8,334,644 | B2 | 12/2012 | Ramer et al. |
| 8,398,264 | B2 | 3/2013 | Anderson et al. |
| 2008/0013335 | A1* | 1/2008 | Tsutsumi ............. B60Q 1/2607 362/545 |
| 2011/0307035 | A1* | 12/2011 | Tsao ..................... A61N 5/0616 607/90 |
| 2012/0327656 | A1 | 12/2012 | Ramer et al. |
| 2013/0049602 | A1 | 2/2013 | Raj et al. |
| 2014/0035472 | A1 | 2/2014 | Raj et al. |

OTHER PUBLICATIONS

Koninklijke Philips Electronics N.V., "HealWell—A New Lighting Solution for Patient Rooms", Dec. 2011, http://www.lighting.philips.com/pwc_li/main/application_areas/assets/pdf/healwell-brochure-int.pdf.

Lighting Research Center, "Red Light Increases Alertness During 'Post-Lunch Dip'", Apr. 22, 2013, http://www.lrc.rpi.edu/resources/newsroom/pr_story.asp?id=253.

Photonics.com, "CLEO Presents Cutting-Edge Research on Optics, Lasers", Jun. 7, 2013, http://www.photonics.com/Article.aspx?AID=54092.

Airocide.com, 2013, https://www.airocide.com/.

Tuner, Jan, "Laser Destistry/Low Level Laser Therapy: Therapeutic Lasers Expand the Scope of Dentistry", Sep. 1, 2010, http://www.biboopticsworld.com/articles/print/volume-3/issue-5/features/laser-dentistry-low-level-laser-therapy-therapeutic-lasers-expand-the-scope-of-dentistry.html.

Goode, Barbara, "Laser Light Therapy/Hair Restoration: Crowdfunding Succeeds for At-Home Laser Hair-Growth Device", Sep. 25, 2013, http://www.biboopticsworld.com/articles/print/volume-6/issue-5/departments/news-notes/laser-light-therapy-hair-restoration-crowdfunding-succeeds-for-at-home-laser-hair-growth-device.html.

FAWK3S, Finding Blood with UV Light, Mar. 20, 2010, http://www.physicsforums.com/showthread.php?t=288224, 5 pages.

Noureddine, Maher, Forensic Tests for Semen: What you Should Know, Oct. 10, 2011, http://ncforensics.wordpress.com/2011/10/19/forensic-tests-for-semen-what-you-should-know/, 5 pages.

\* cited by examiner

COMBINATORIAL LIGHT DEVICE FOR GENERAL LIGHTING AND LIGHTING WITH BENEFICIAL WAVELENGTHS

TECHNICAL FIELD

The examples discussed below relate to techniques and equipment to provide a light source for general illumination of a space and an additional light source to provide light of a particular wavelength at an intensity and for a duration expected to be sufficient to support a benefit (e.g., treatment of medical conditions, vitamin growth, etc.) other than general illumination of the space, with both light sources being integrated into a single lighting device.

BACKGROUND

In recent years, demand has arisen for lighting systems that produce light for purposes other than general illumination. Multiple lighting devices are used for such different alternative purposes. For example, many lights are designed to produce only a particular wavelength of light, such as ultraviolet, infrared, or particular wavelengths of visible light with an increased intensity versus that of general illumination lights. Many benefits are associated with lights of particular wavelengths, such as vitamin growth, plant growth, sanitation, medical treatment, and the like.

The need to produce these additional wavelengths at sufficient intensities leads to many applications where multiple lighting fixtures are used. Users will often have a device for general illumination, and an additional device for generating the preferred wavelength of light that is used for the associated benefits. The requirement to have multiple devices is not convenient in most applications. For example, installation of multiple lighting fixtures in a single room may not be operable as the room may not be designed to incorporate more than one lighting device. Also, in the medical context, using multiple lighting fixtures can lead to the discomfort of patients having to be exposed to light that substantially alters the appearance of their surroundings (e.g., using a green 540 nm light for Mastocytosis treatment will turn the entire room green).

SUMMARY

Hence a need exists for a single lighting device that can generate light for general illumination and can generate light of one or more particular wavelengths that may support an intended benefit other than general illumination. A further need exists for such lighting devices with the capability to generate the light of the particular beneficial wavelength(s) at a sufficient intensity, sufficient duration, and/or proper characteristic expected to effectively support such benefits, while being capable of simultaneously or independently producing light for general illumination of a space.

The equipment and techniques disclosed herein address one or more of the above noted problems or needs with respect to multiple lighting devices for producing light of particular wavelengths associated with achieving intended benefits other than general illumination of a space when output at sufficient intensities, durations, and characteristics.

As disclosed herein, examples of lighting devices include a first light source configured to generate light for illumination of a space and a second light source configured to generate light of a particular wavelength independently from the first light source. The light generated by the second light source is output at a sufficient intensity so as to support an intended benefit other than illumination of the space. Additionally, the first light source and the second light source are integrated into the same lighting device. Further, in one example, the lighting devices include an optical element, such as a light integrating cavity, coupled to the first and second light sources that is configured to produce a light output of the lighting device. The lighting devices in the examples output the light for illumination of the space from the first light source and the light of the particular wavelength for the other intended benefit from the second light source via the light output of the lighting device.

Other examples of lighting devices include a light source configured to project light toward a pixelated screen. The pixelated screen may include a first section of pixels and a second section of pixels. In the example, the first section of pixels generates and outputs light for illumination of a space after receiving light projected from the light source. The second section of pixels generates and outputs light of a particular wavelength independently from the first section after receiving light projected from the light source. Further, the lighting device outputs the light of the particular wavelength at a sufficient intensity reasonably expected to support an intended benefit other than general illumination of the space.

Methods of lighting a space are also disclosed herein by way of examples. Such a method example includes generating light for illumination of the space from a first light source and generating light of a particular wavelength with a second light source independently from the light for illumination of the space. Further, in an example, the first and second light source are integrated into the same lighting device. In addition, the light for illumination and the light of the particular wavelength can be combined with a light cavity and outputted via a light output of the lighting device. The light of the particular wavelength is of a sufficient intensity to support an intended benefit other than illumination of the space.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various examples disclosed herein relate to lighting devices, each with a light source for general illumination of a space and a light source for generating light of a particular wavelength that supports an intended benefit other than general illumination of the space when output at a sufficient intensity for a sufficient duration, and/or output with another particular characteristic, such as in a flashing pattern. Techniques for operating one or more such light devices to provide both general illumination and output of one or more beneficial wavelengths are also discussed in the description below.

The disclosed lighting devices and lighting systems include a light source for general illumination and a light source for generating beneficial wavelengths, with both light sources integrated into the same device. The light sources for generating beneficial wavelengths are constructed to generate and output light of a particular wavelength at one or more of: sufficient intensities, durations, change rates or the like, for the intended or desired benefit other than general illumination. The lighting devices may include lighting fixtures, such as ceiling fixtures, table lamps, desk lamps, etc., as well as lighting systems such as medical lighting devices. It will be understood that the disclosed lighting devices can be implemented in various types of lighting fixtures, lighting systems, and other lighting apparatus.

Figure 1:
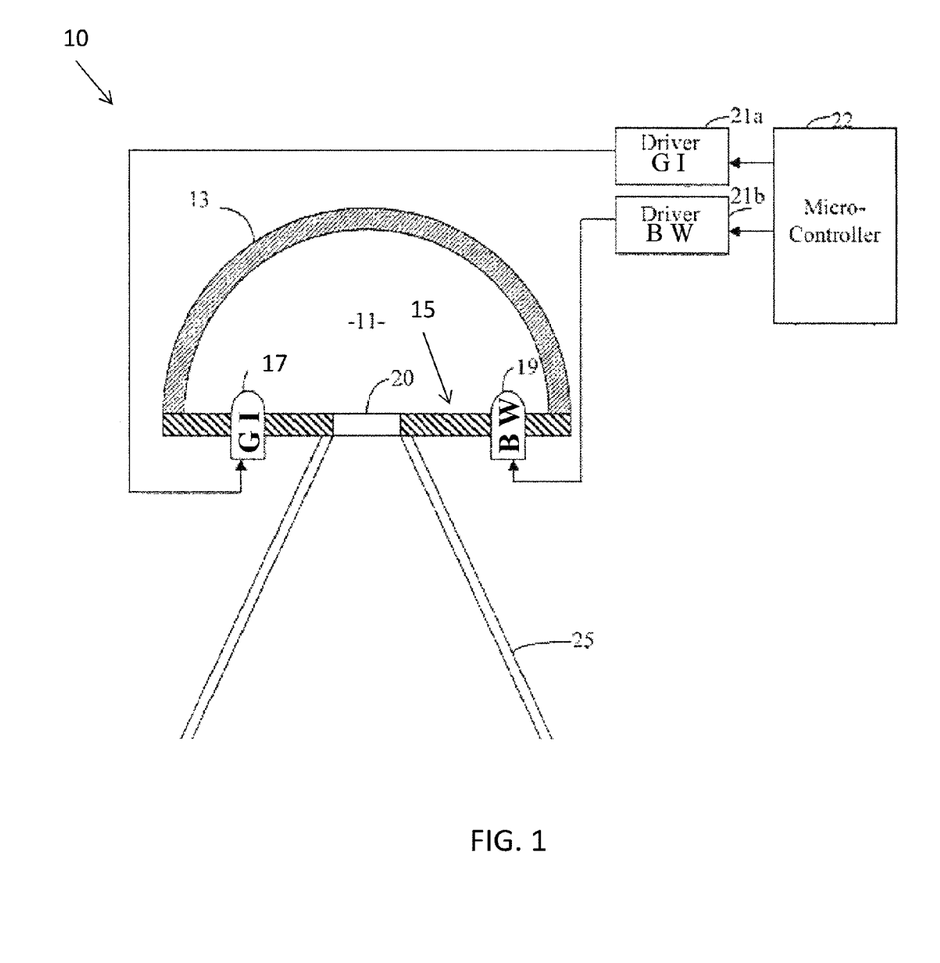
FIG. 1 illustrates an example of a lighting device for general illumination as well as illumination with one or more beneficial wavelengths, with certain elements thereof shown in cross-section.

Reference now is made in detail to the examples illustrated in the accompanying drawings and discussed below. FIG. 1 illustrates a cross-sectional illustration of a lighting device or system 10. The device or system 10 is intended for general lighting applications in areas or regions intended to be occupied by one or more persons who will see by the light provided by the systems, and for outputting light of a particular wavelength at a sufficient intensity and for a sufficient duration reasonably expected to achieve an intended benefit other than general illumination. For example, for task lighting applications, the device outputs light in the visible spectrum for general illumination, but may also output light of the particular wavelength(s) for the beneficial purpose simultaneously to and independent from the general illumination.

There may be some difference of opinion among technical practitioners as to the light characteristics needed to achieve a particular benefit, e.g. the duration and intensity of exposure to particular wavelength band light needed to support a particular benefit. The technologies under discussion here are intended to deliver light for a general illumination purpose and light of wavelength(s) for a beneficial purpose from a device integrating sources for both purposes and typically through the same output path of the device.

Although the light characteristics are intended to support the beneficial purpose, the present disclosure is not limited either to any particular standard or magnitude of lighting parameters that different authorities may feel are required to fully achieve a particular desired or intended benefit other than general illumination.

Furthermore, it will be understood the intended benefit that a disclosed example of such a device is reasonably expected to support may not be fully achieved due to circumstances unrelated to the operation of the lighting device. For example, in medical applications, the benefit may require a patient to remain exposed to the particular wavelength for a given time. The benefit may not be fully achieved in the event of the patient leaving the exposure field of the particular wavelength or a doctor prematurely terminating exposure prior to achieving the benefit. As another therapeutic example, one medical study may suggest a particular parameter (e.g. intensity or duration) is required, whereas another authority may suggest a higher or lower value of the particular parameter is needed to achieve the benefit. Thus, the benefit may not be fully achieved in the event that the studies are followed and either study is incorrect or incomplete as to the particular parameters. The devices disclosed herein are capable of emitting particular wavelengths at a sufficient intensity, sufficient duration, and/or otherwise proper characteristic to at least partially achieve an intended benefit absent unrelated interfering circumstances, and are thus reasonably expected to support the intended benefit. For many beneficial wavelength emission(s), the emissions of the appropriate wavelength(s) will exhibit a sufficient intensity to support the intended benefit and will exhibit one or more other characteristics of sufficient values to support the particular benefit, such as a sufficient one or more of: duration, intensity variation rate (e.g. flicker rate).

In the lighting device examples, each lighting device includes an optical element coupled to receive light from the sources and configured to provide an output of light for the device, where light from both sources emerge via the same device output. The two types of light from the light sources may be output at different times, or in other examples, the two types of light emerge via the same output more or less simultaneously. Many of the examples of the lighting devices therefore include a type of optical element that serves to combine light from multiple light sources integrated within the respective lighting device.

Hence, a system like device 10 combines light from multiple sources, and for that purpose, most examples of lighting devices include an optical light mixer, such as a diffuser. In the example of FIG. 1, the illustrated system 10 includes an optical cavity 11 having a diffusely reflective interior surface to receive and combine radiant energy of different colors/wavelengths. The cavity 11 may have various shapes. The illustrated cross-section would be substantially the same if the cavity is hemispherical or if the cavity is semi-cylindrical with the cross-section taken perpendicular to the longitudinal axis. The optical cavity in the examples discussed below is typically an optical integrating cavity.

The disclosed devices may use a variety of different structures or arrangements for the optical integrating cavity. At least a substantial portion of the interior surface(s) of the cavity exhibit(s) diffuse reflectivity. It is desirable that the cavity surface have a highly efficient reflective characteristic, e.g. a reflectivity equal to or greater than 90%, with respect to the relevant wavelengths. In the example of FIG.

1, the surface is highly diffusely reflective to energy in the visible, near-infrared, and ultraviolet wavelengths.

The cavity 11 may be formed of a diffusely reflective plastic material, such as a polypropylene having a 97% reflectivity and a diffuse reflective characteristic. For purposes of the discussion, the cavity 11 in the device 10 is assumed to be hemispherical. In the example, a hemispherical dome 13 and a substantially flat cover plate 15 form the optical cavity 11. At least the interior facing surfaces of the dome 13 and the cover plate 15 are highly diffusely reflective, so that the resulting cavity 11 is highly diffusely reflective with respect to the radiant energy spectrum produced by the device 10. As a result, the cavity 11 in the example of FIG. 1 is an integrating type optical cavity. Although shown as separate elements, the dome and plate may be formed as an integral unit.

The optical integrating cavity 11 has an optical aperture 20 (e.g., an output) for allowing output of combined light energy (e.g., the combined general illumination light and the beneficial wavelength light). In the example, the aperture 20 is a passage through the approximate center of the cover plate 15, although the aperture may be at any other convenient location on the plate 15 or the dome 13. Although a single aperture is depicted, it is contemplated that the lighting devices may have multiple apertures, such as an LCD shutter array as described below. The aperture is transmissive to light. Although shown as a physical passage or opening through the wall or plate of the cavity, those skilled in the art will appreciate that the optical aperture may take the form of a light transmissive material, e.g. transparent or translucent, at the appropriate location on the structure forming the cavity 11.

Because of the diffuse reflectivity within the cavity 11, light within the cavity is integrated before passage out of the optical aperture 20. In the examples, the device 10 is shown outputting the combined light downward through the aperture 20, for convenience. However, the device 10 may be oriented in any desired direction to perform a desired application function, for example, to provide general illumination and other beneficial lighting to persons in a particular direction or location with respect to the lighting device 10 or to illuminate or provide beneficial wavelength(s) to a different surface such as a wall, floor, desk, bed or table top.

Also, the optical integrating cavity 11 may have more than one aperture 20, for example, oriented to allow output of integrated light in two or more different directions or regions. The device 10 and/or the aperture(s) 20 may additionally be oriented or positioned such that the light of the particular wavelength for the intended benefit is outputted in a particular direction or location with respect to the lighting device or outputted to target a different surface such as a wall, floor, table, or other object in the room, such as a hospital bed or a body part of a human.

In the example, the cavity 11 appears empty, e.g. as if filled with air. It is also contemplated that a wide range of other cavity structures may be used, including structure in which the cavity is partially filled with an optically transmissive liquid or solid. In that regard, just a few of many examples of other lighting device arrangements with alternative cavity structures may be found in U.S. Pat. Nos. 8,282,241; 8,172,424; 8,205,998 and 8,021,008, the full patent disclosures of which are incorporated entirely herein by reference.

Light sources 17 to 19 supply light into the interior of the optical integrating cavity 11 and are both integrated into the device 10. Light source 17 generates light for general illumination (GI) of a space and light source 19 generates light of a particular wavelength (e.g., a beneficial wavelength (BW)) for a benefit other than general illumination of the space. The cavity 11 effectively integrates the energy of the GI light and the BW light so that the integrated or combined light energy outputted through the aperture 20 includes the radiant energy of the GI light and the BW light in relative amounts substantially corresponding to the relative intensities of input into the cavity 11.

For simplicity, the example shows a single source of each type. Depending on the technology and/or the variety of beneficial wavelengths offered by the device 10, there may be any number of each type of light source. The general illumination source 17 may be implemented using one or more emitters of white light, a combination of emitters of white light and emitters of light intended to adjust or improve the color characteristic(s) of the white light or by a number of sources of different colors (e.g. red, green and blue) that can be combined by the cavity 11 to produce light that is sufficiently white to support the general illumination function of the device 10. Each included beneficial wavelength source 19 emits light of some wavelength range about a nominal rated wavelength, e.g. around 540 nanometers (nm), around 1300 nm, about a nominal wavelength in the 320-340 nm, around 207 nm, around 260 nm, and/or other wavelengths reasonably expected to support a benefit other than general illumination when outputted at a sufficient intensity or with other sufficient characteristic(s).

Control of the intensity of output of the GI light source 17 and the BW light source 19 sets a spectral characteristic of the combined GI light and the BW light outputted through the aperture 20 of the optical integrating cavity. Although other types of light emitters may be used for either one or both of the sources 17, 19, for purposes of further discussion, we will assume that each source 17 or 19 utilizes one or more light emitting diodes (LEDs).

The microcontroller 22 may be responsive to a number of different control input signals. For example, microcontroller 22 may be responsive to one or more user inputs of various types. Further, the microcontroller 22 may be responsive condition sensors, e.g. providing information relating to feedback about operations the LED light sources 17 to 19 and/or sensing conditions of lighting or objects in the space to be illuminated by the device. Feedback may be provided through the photo sensing device (not shown), for example, to detect overall intensity of light output or information about color characteristics of light in the cavity or output via the aperture. Depending on the application of the device 10, different types of optical feedback sensing may be provided, relative to light generated for illumination and/or beneficial wavelength light. It may also be desirable to sense temperature of or around one or both light sources. Other condition sensors may provide input information about one or more conditions in the illuminated space. Although not shown, a sensor, for example, might detect occupancy; whereas another sensor might detect ambient light level.

The device 10 includes a driver 21a for the GI light source 17 and a driver 21b for the BW light source 19. The drivers 21a and 21b may be controlled independently from one another, although they may be operated to selectively turn ON the respective sources at different times and/or simultaneously with one another. GI driver 21a controls the intensity, duration, and other characteristics (e.g., frequency of variation of output intensity) of the GI light generated from the GI light source 17. If the source 17 produces light for general illumination of different color characteristics, e.g. tunable white, the driver 21a may also adjust source 17 to deliver different color light. The BW driver 21b controls the intensity, duration, and other characteristics (e.g., ON/OFF frequency of variation of output intensity) of the BW light generated from the BW light source 19. Drivers 21a and 21b may be controlled by the microcontroller 22, timers, and/or by a user input. Driver 21b is configured to control the intensity and the duration of BW light output from the BW light source 19 so as to reasonably expect to support the intended benefit other than general illumination.

The aperture 20 may serve as the final output of the lighting device 10. In the example, the device includes a secondary optic. Although various secondary optics may be used, such as lenses, diffusers, filters or the like, the example utilizes a reflector to effectively direct the light output from the aperture 20 over a desired field of illumination. The reflector may have other shapes or be formed in other ways, but in the example, the reflector is formed by conical reflector 25.

The conical reflector 25 may have a variety of different shapes, depending on the particular lighting application. In the example, where cavity 11 is hemispherical, the cross-section of the conical reflector is typically circular. However, the reflector may be somewhat oval in shape. In applications using a semi-cylindrical cavity, the reflector may be elongated or even rectangular in cross-section. The shape of the aperture 20 also may vary, but will typically match the shape of the small end opening of the reflector 25. Hence, in the example, the aperture 20 would be circular. However, for a device with a semi-cylindrical cavity and a reflector with a rectangular cross-section, the aperture may be rectangular.

Control of the intensity, duration and other characteristics of the BW light outputted from the BW light source 19 ensures that the intended benefit other than general illumination of the space is supported and will most likely be achieved absent unrelated interfering circumstances. The intensity and the duration of the BW light may be predetermined in the lighting device 10, or may be controlled (e.g., via driver 21b, microcontroller 22, user input, etc.) independently of control of the GI light output, so as to support the benefit and be reasonably expected to achieve the benefit in a desired place and time. When BW lighting is provided for a particular benefit, the wavelength(s) for the benefit are output at the intensity and having any other characteristics appropriate to the particular benefit. If both GI and BW light output are provided simultaneously, and there is a spectral overlap of the GI light and the BW light, the controller may adjust the characteristics of either one or both types of light output accordingly, e.g. so that the combined light provides the characteristics at the BW wavelength(s) for the particular beneficial purpose while maintaining as must as possible desirable lighting characteristics for GI purposes.

Figure 2:
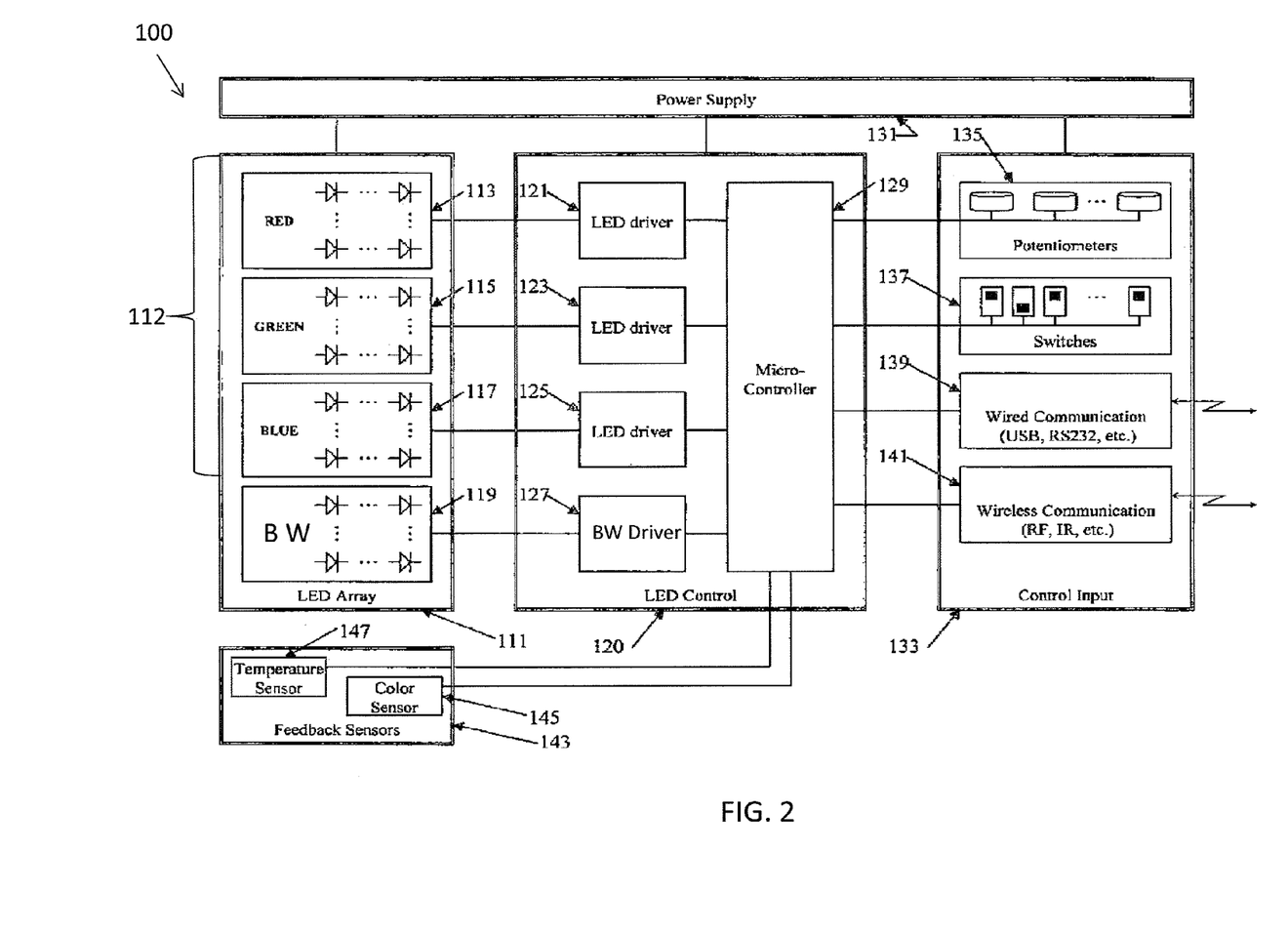
FIG. 2 is a functional block diagram of electrical components of a lighting device for generating general illumination light and for generating particular wavelengths that support an intended benefit other than general illumination of a space.

FIG. 2 is a block diagram of exemplary circuitry for the sources and associated control circuit, providing digital programmable control, which may be utilized with a lighting device of the type described above. In this circuit example, the sources of radiant energy of the various types together form an LED array 111. Although white LEDs or combinations of white and other colors of LEDs may be used as a general illumination light source 112, the example uses LEDs of several different colors to provide the general illumination. Hence, array 111 comprises two or more LEDs of each of the three primary colors, red green and blue, represented by LED blocks 113, 115 and 117. For example, the array may comprise six red LEDs 113, three green LEDs 115 and three blue LEDs 117. The LED blocks 113, 115, and 117 make up the light source 112 for general illumination (e.g., GI light) of a space.

The LED array in this example also includes a number of additional or "other" LEDs 119 that make up the light source for generating light of a particular wavelength (e.g., BW light). There are several types of additional LEDs that are of particular interest in the present discussion. One type of additional LED provides one or more additional wavelengths of radiant energy for each beneficial purpose to be supported by operation of the device 10, for integration within the cavity 11. The additional wavelengths may be in the visible portion of the light spectrum. Alternatively, the additional wavelength LEDs may provide energy in one or more wavelengths outside the visible spectrum, for example, in the infrared range or the ultraviolet range. The additional wavelengths generated by the BW light source 119 are particular and are of a sufficient intensity and duration to support an intended benefit other than general illumination of the space as is the light produced by the GI light source 112.

Another type of alternative or additional LED of interest is a white LED. For white lighting applications, one or more white LEDs provide increased intensity. The primary color LEDs then provide light for color adjustment and/or correction of the GI light generated by the GI light source 112. The white LED may also be used for adjustment and/or correction of the BW light generated by the BW light source 119.

The electrical components shown in FIG. 2 also include an LED control system 120. The system 120 includes driver circuits for the various LEDs and a microcontroller. The driver circuits supply electrical current to the respective LEDs 113 to 119 to cause the LEDs to output light. The driver circuit 121 drives the red LEDs 113, the driver circuit 123 drives the green LEDs 115, and the driver circuit 125 drives the blue LEDs 117. In this example using three types of LEDs to implement the GI source, the driver circuits 121, 123, and 125 make up the general illumination driver (GI driver) for the GI light source 112. In a similar fashion, when active, the beneficial wavelength driver circuit (BW driver) 127 provides electrical current to the BW LEDs 119. If the other LEDs provide another color of light, and are connected in series, there may be a single driver circuit 127. The intensity of the outputted light of a given LED is related to the level of current supplied by the respective driver circuit. As such, the BW driver 127 is configured to supply sufficient current to the BW light source 119 such that the intended benefit of the BW light is supported.

The current output of each driver circuit is controlled by the higher level logic of the system. In this digital control example, that logic is implemented by a programmable microcontroller 129, although those skilled in the art will recognize that the logic could take other forms, such as discrete logic components, an application specific integrated circuit (ASIC), etc.

The LED driver circuits and the microcontroller 129 receive power from a power supply 131, which is connected to an appropriate power source (not separately shown). For most task-lighting applications, the power source will be an AC line current source, however, some applications may utilize DC power from a battery or the like. The power supply 129 converts the voltage and current from the source to the levels needed by the driver circuits 121-127 and the microcontroller 129.

A programmable microcontroller typically includes or has coupled thereto random-access memory (RAM) for storing data and read-only memory (ROM) and/or electrically erasable read only memory (EEROM) for storing control programming and any pre-defined operational parameters, such as pre-established light 'recipes.' The microcontroller 129 itself comprises registers and other components for implementing a central processing unit (CPU) and possibly an associated arithmetic logic unit. The CPU implements the program to process data in the desired manner and thereby generate desired control outputs.

The microcontroller 129 is programmed to control the LED driver circuits 121-125 to set the individual output intensities of the LEDs 113-117 to desired levels, so that the light generated from the GI light source 112 from the aperture of the cavity has a desired spectral characteristic and a desired overall intensity. The microcontroller 129 is also programmed to control the BW driver 127 independently from and/or simultaneously to the GI drivers 121-125, such that the BW light generated by LEDs 119 is of a sufficient intensity, is output for a sufficient duration, and/or has the appropriate characteristics so as to support the desired benefit of the BW light. The microcontroller 129 may be programmed to essentially establish and maintain or preset a desired 'recipe' or mixture of the available wavelengths provided by the LEDs used in the particular system, at different times or under different conditions and/or for different operational purposes. For example, there may be one or several such recipes for general lighting and one or more for each beneficial lighting purpose supported by the particular implementation of the lighting device. The microcontroller 129 receives control inputs specifying the particular 'recipe' or mixture, as will be discussed below. To insure that the desired mixture is maintained for the GI light, the microcontroller may receive a color feedback signal from an appropriate color sensor. The microcontroller may also be responsive to a feedback signal from a temperature sensor, for example, in or near the optical integrating cavity.

The electrical system will also include one or more control inputs 133 for inputting information instructing the microcontroller 129 as to the desired operational settings. A number of different types of inputs may be used, and several alternatives are illustrated for convenience. A given installation may include a selected one or more of the illustrated (or other) control input mechanisms.

As one example, user inputs may take the form of a number of potentiometers 135. The number would typically correspond to the number of different light wavelengths provided by the GI light source 112 and the particular beneficial wavelength provided by the BW light source 119. The potentiometers 135 typically connect through one or more analog to digital conversion interfaces provided by the microcontroller 129 (or in associated circuitry). To set the parameters for the GI light, the user adjusts the potentiometers 135 to set the intensity for each color in the GI light source 112. Correspondingly, a user may adjust the potentiometers 135 to activate the BW light source 119, and/or to set the desired intensity, duration, and characteristic of the BW light to support the intended benefit of the particular beneficial wavelength. The microcontroller 129 senses the input settings and controls the LED driver circuits accordingly to set corresponding intensity levels for the LEDs providing the light for general illumination and the light of the particular beneficial wavelength.

Another user input implementation might utilize one or more dip switches 137. For example, there might be a series of such switches to input a code corresponding to one of a number of recipes. The memory used by the microcontroller 129 would store the necessary intensity levels for the different color LEDs in the GI light source 112 for each recipe. Based on the input code, the microcontroller 129 retrieves the appropriate recipe from memory. Then, the microcontroller 129 controls the GI LED driver circuits 121-125 accordingly, to set corresponding intensity levels for the LEDs 113-117 providing the light for general illumination of the space. The microcontroller 129 may operate similarly for independent activation and control of the BW light source 119 and the BW driver 127 to generate light of the particular beneficial wavelength.

As an alternative or in addition to the user input in the form of potentiometers 135 or dip switches 137, the microcontroller 129 may be responsive to control data supplied from a separate source or a remote source. For that purpose, some versions of the system will include one or more communication interfaces. One example of a general class of such interfaces is a wired interface 139. One type of wired interface typically enables communications to and/or from a personal computer or the like, typically within the premises in which the fixture operates. Examples of such local wired interfaces include USB, RS-232, and wire-type local area network (LAN) interfaces. Other wired interfaces, such as appropriate modems, might enable cable or telephone line communications with a remote computer, typically outside the premises. Other examples of data interfaces provide wireless communications, as represented by the interface 141 in FIG. 2. Wireless interfaces, for example, use radio frequency (RF) or infrared (IR) links. The wireless communications may be local on-premises communications, analogous to a wireless local area network (WLAN). Alternatively, the wireless communications may enable communication with a remote device outside the premises, using wireless links to a wide area network.

As noted above, the electrical components may also include one or more feedback sensors 143, to provide system performance measurements as feedback signals to the control logic, implemented in this example by the microcontroller 129. A variety of different sensors may be used, alone or in combination, for different applications. In the illustrated examples, the set 143 of feedback sensors includes a color sensor 145 and a temperature sensor 147. Although not shown, other feedback sensors, such as an overall intensity sensor may be used. Alternatively or in addition, the system may include external condition sensors, for example, to sense ambient light level and/or color characteristics or to sense occupancy. The feedback and/or external condition sensors are positioned in or around the system to measure the appropriate physical condition, e.g. temperature, color, intensity, etc.

The color feedback sensor 145, for example, is coupled to detect color distribution in the integrated radiant energy. The color sensor may be coupled to sense energy within the optical integrating cavity, within the deflector (if provided) or at a point in the field illuminated by the particular system. Various examples of appropriate color sensors are known. If mainly used for feedback sensing relative to the general lighting illumination, the sensor 145 might be an RGB color sensor such as a Hamamatsu style RGB color sensor. Another suitable sensor might use the quadrant light detector disclosed in U.S. Pat. No. 5,877,490, with appropriate color separation on the various light detector elements (see U.S. Pat. No. 5,914,487 for discussion of the color analysis). Alternative or additional sensors may be provided for sensing light in one or more wavelength ranges from the BW LEDs 119.

The associated logic circuitry, responsive to the detected color distribution, controls the output intensity of the GI light and controls the BW light independently from the GI light, so as to provide a desired color distribution in the integrated radiant energy for general illumination of the space, as well as beneficial wavelengths of sufficient intensity, duration, and characteristic for supporting the intended benefit other than general illumination of the space, in accord with appropriate settings. The color sensor measures the color of the integrated radiant energy produced by the system and provides a color measurement signal to the microcontroller 129.

The temperature sensor 147 may be a simple thermoelectric transducer with an associated analog to digital converter, or a variety of other temperature detectors may be used. The temperature sensor is positioned on or inside of the fixture, typically at a point that is near the LEDs or other sources that produce most of the system heat. The temperature sensor 147 provides a signal representing the measured temperature to the microcontroller 129. The system logic, here implemented by the microcontroller 129, can adjust intensity of one or more of the LEDs in response to the sensed temperature, e.g. to reduce intensity of the source outputs to compensate for temperature increases.

Beneficial wavelengths (BWs) include wavelengths that, when output at a sufficient intensity, for a sufficient duration, and/or with a particular characteristic, support a benefit other than general illumination of the space. The benefits are desirable in various industries. The benefits may include therapeutic benefits. Therapeutic benefits are those of which a therapeutic effect may be achieved for a human or other biological entity upon exposure to the BWs, under conditions deemed appropriate. For example, exposure to light at a wavelength of about 540 nm at sufficient intensity for a sufficient period may provide symptom relief for those with Mastocytosis, exposure to ultraviolet light at wavelengths of about 320-340 nm at sufficient intensity for a sufficient period may promote vitamin D growth and can be used to simulate exposure to outdoor environments, exposure to infrared wavelengths at about 1300 nm at sufficient intensity for a sufficient period may promote wound healing, exposure to blue light at sufficient intensity and for a sufficient period may promote/suppress hormone production (e.g., melatonin suppression) in a human, exposure to light at a wavelength of 207 nm can destroy drug-resistant bacteria, exposure to certain wavelengths promotes plant growth and/or entrains plants to different parts of growth cycles (e.g., blooming, hibernation, etc.), etc. The benefits may also include diagnosis benefits such that diagnosis of a condition might be made more easily or accurately through exposure of a plant or a body part to particular wavelengths of a sufficient intensity and/or duration. The benefits may also include detection benefits. Exposing a space to particular wavelengths can illuminate dust, blood, and other chemicals, contaminants, or foreign substances/objects present in the space. Furthermore, objects in a space can be caused to appear to flash based on the optical characteristics of the objects and exposure to light of a particular wavelength when outputted in a pattern of a particular frequency. Infractions in infrastructures (e.g., cracks or other damage to buildings, submarines, etc.) can also be detected upon exposure to light of a particular wavelength. The benefits may also include sanitation by exposing a space to high intensity levels of light of ultraviolet wavelengths (e.g., about 260 nm). The above described benefits are exemplary and not exclusive. It will be understood that the lighting devices disclosed are capable of both generating and outputting light for general illumination as well as generating and outputting light of various particular wavelengths at sufficient intensities, durations, intensity variation rates or the like, in support of one or more of numerous benefits instead of or in addition to the examples described herein.

Figure 3:
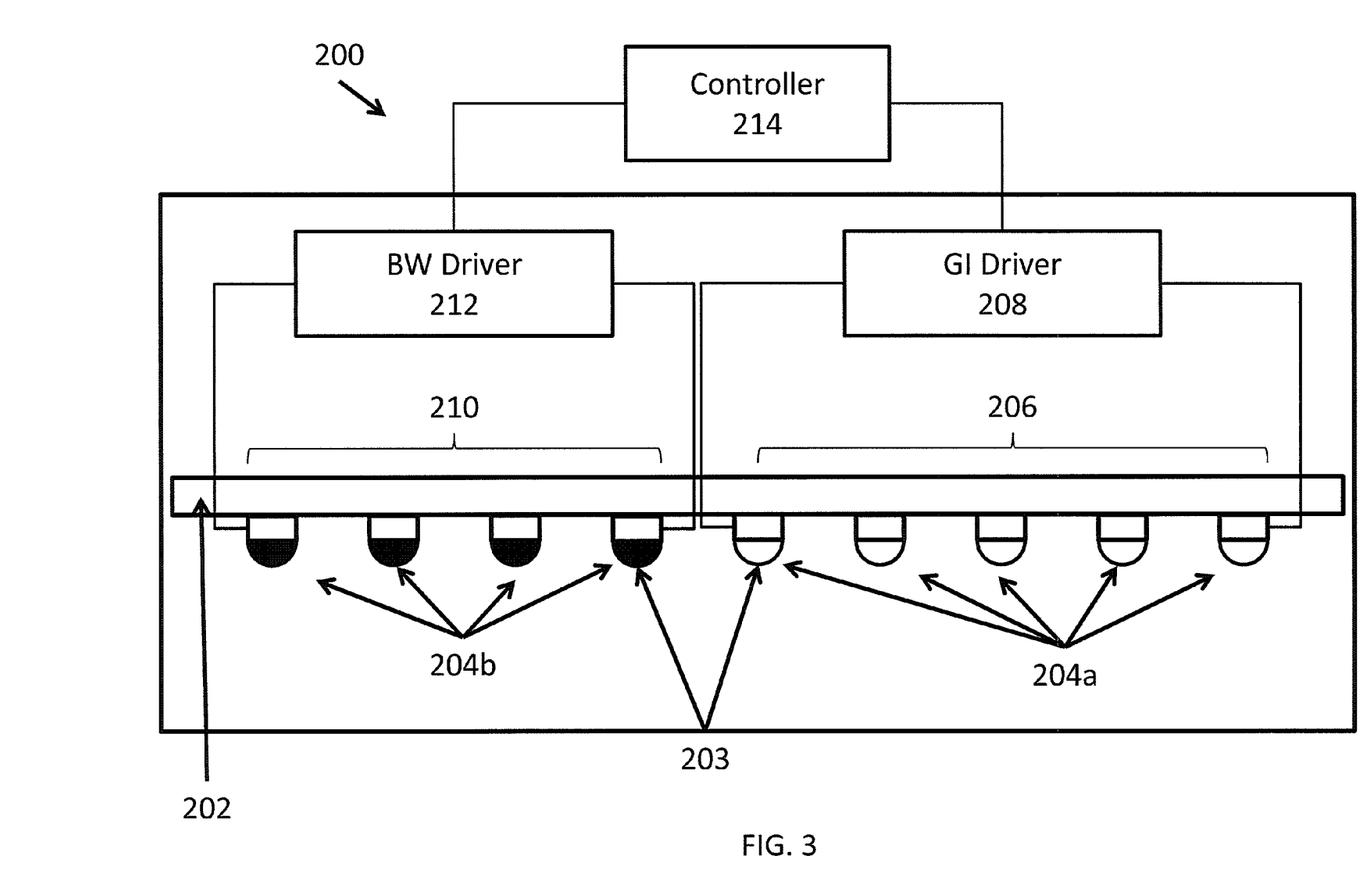
FIG. 3 is a diagram showing an example of a lighting device for generating beneficial wavelengths with a dimming mechanism.
Figure 4:
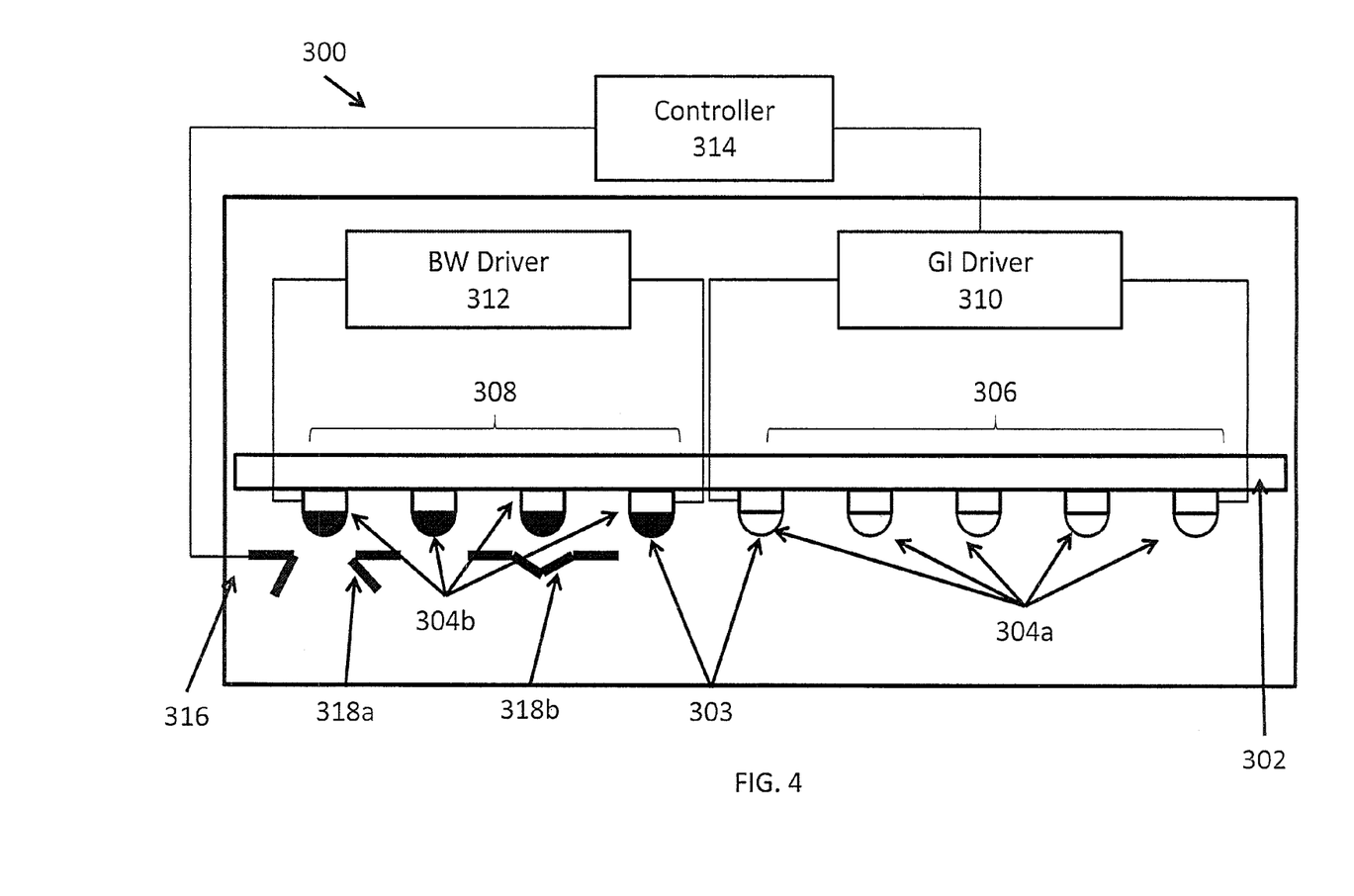
FIG. 4 is a diagram showing an example of a lighting device for generating beneficial wavelengths with shutter mechanisms.
Figure 5:
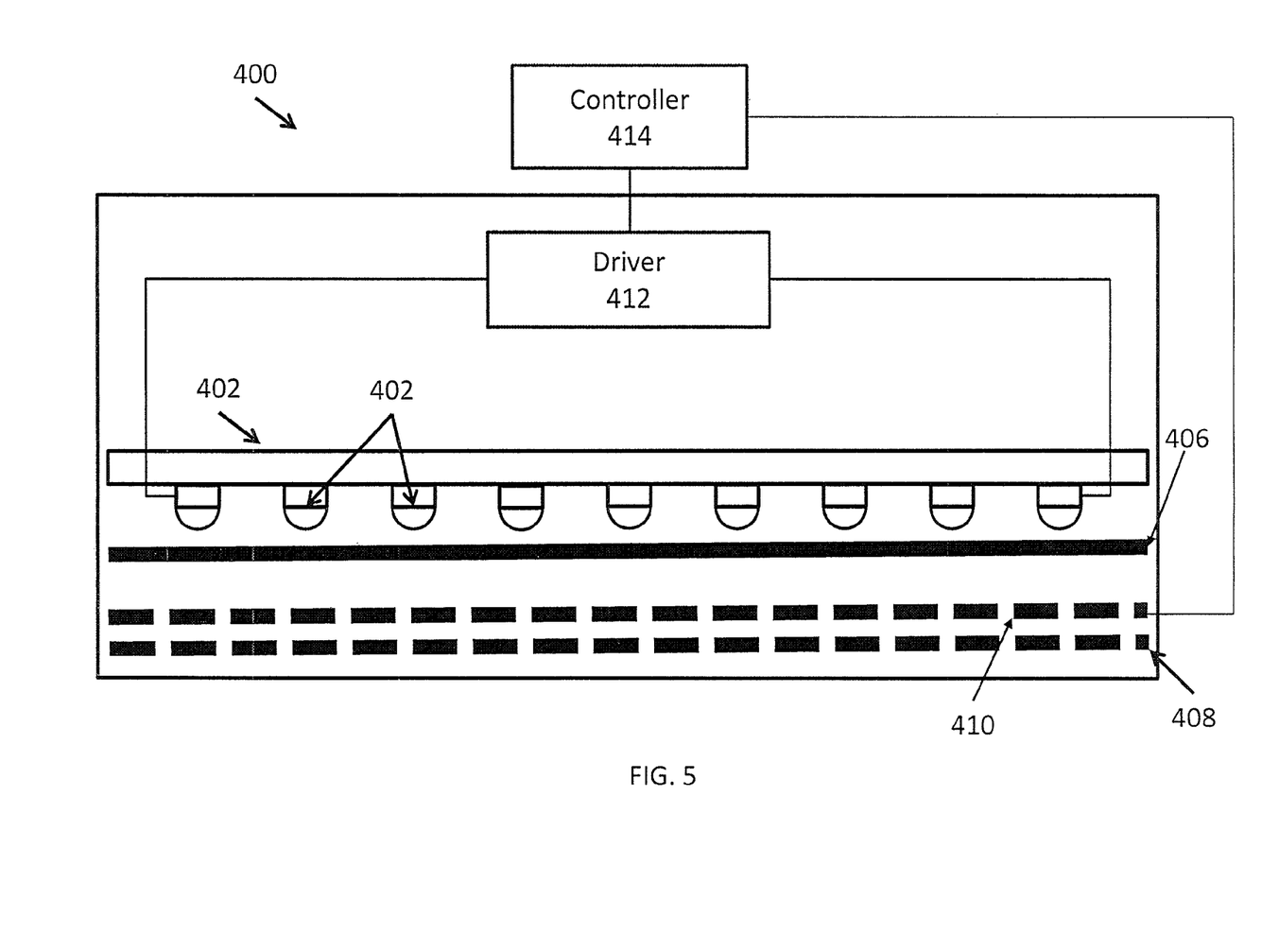
FIG. 5 is a diagram showing an example of a lighting device for generating beneficial wavelengths with a pixelated screen and an LCD shutter array.

Additional examples of mechanisms for producing light for general illumination and beneficial wavelengths with the lighting devices are depicted in FIGS. 3-5. For convenience of illustration, these illustrations show examples of lighting devices positioned to output light downward, e.g. from a ceiling fixture or drop-light type installation. As with the earlier examples, the examples in FIGS. 3-5 may be positioned or oriented to output light in other directions as suitable for particular lighting applications and/or installations.

FIG. 3 shows an example of a lighting device utilizing a dimming mechanism. The lighting system 200 includes an array 202 of LEDs 203. The array 202 is partitioned into a general illumination (GI) section 206 coupled to a general illumination (GI) driver 208 and a beneficial wavelength (BW) section 210 coupled to a beneficial wavelength (BW) driver 212. The GI section 206 functions as the GI light source and the BW section 210 functions as the BW light source for the lighting device 200. A controller 214 is coupled to the GI driver 208 and the BW driver 212 and the drivers 210 and 212 operate in response to the controller 214. The controller 214 operates the BW driver 212 independently from and/or simultaneously to the GI driver 208. The controller 214 may operate the drivers 210 and 212 based on predetermined settings, timers, and/or user input. The drivers and controller may be implemented in a manner similar to the drivers and controllers in the earlier examples. For convenience, the optical elements coupled to the sources so as to supply both types of light to the device output are not shown specifically in this drawing.

The LEDs 204a on the GI section 206 produce light for general illumination of a space, and may be configured and arranged to produce fixed white light, tunable white light, RGB, etc. The LEDs 204b on the BW section 206 produce light of a particular wavelength to support a benefit other than general illumination of the space. In the example illustrated in FIG. 3, the BW driver 212 implements a dimming mechanism such that, in response to a corresponding signal from the controller 214, the BW driver 212 decreases the brightness and intensity of the BW LEDs 204b independently from the GI LEDs 204a when the intended benefit of the BW is not desired. The brightness and intensity of the GI LEDs 204a can be maintained and, thus, GI light is emitted, illuminating the space. When the benefit of the BW light is desired, the BW driver 212, in response to a corresponding signal from the controller 214, increases the brightness and intensity of the BW LEDs 204b to a sufficient level, and the intensity of the BW LEDs 204b is maintained for a sufficient duration so as to support the benefit of the BW. When the benefit of the BW is desired and the intensity of the BW LEDs 204b is increased, the brightness and intensity of the GI LEDs 204a may be independently maintained, such that both general illumination of the space and the output of BWs in support of the intended benefit are provided simultaneously. In such examples, the light generated by the BW section 208 may have little effect on the appearance of the light generated by the GI section 206. As an example in a lighting system, such as device 200 and/or other lighting devices disclosed herein, manufactured for general illumination and Mastocytosis treatment, the BW LEDs 204b may produce only green light at a wavelength of 540 nm. In another example, the BW LEDs 204b may produce only ultraviolet light, such that the ultraviolet light output from the BW LEDs 204b would not visibly alter the color of the GI light. The GI driver 210 may also include a dimming mechanism to adjust the brightness of the GI LEDs 204a independently from the BW LEDs 204b and/or a switch to power the GI LEDs 204a ON or OFF independently from the BW LEDs 204b. Thus, it is contemplated that the lighting devices disclosed, such as lighting system 200, may be operable to generate BW light while not generating GI, light, and vice versa.

FIG. 4 depicts another example of a lighting device. The lighting system 300 includes an array 302 of LEDs 303. The array 302 of LEDs 303 is partitioned into a GI section 306 and a BW section 308. A GI driver 310 is coupled to the GI section 306 and a BW driver 312 is coupled to the BW section 308. A controller 314 is coupled to the GI driver 310. The controller 314 may function with respect to GI driver 310 as the controller 214 functions with respect to GI driver 210 described above with regard to FIG. 3. The drivers and controller may also be implemented in a manner similar to the drivers and controllers in the other earlier examples. For convenience, the optical elements coupled to the sources so as to supply both types of light to the device output are not shown specifically in this drawing.

In this example, the controller 314 is also coupled to an array of shutters 316 that are positioned between the BW LEDs 304b and the output (not shown) of the lighting device 300. The shutters 316 may be mechanical shutters, LCD shutters, microelectromechanical (MEM) shutters, etc. Shutter 318a is shown in an open position, allowing BW light generated from a BW LED to pass through the output of the lighting device 300 and be output from the lighting device 300, and shutter 318b is shown in a closed position, blocking BW light generated from a BW LED from passing through the output of the lighting device 300, therefore preventing the BW LED light from being output from the lighting device 300.

In the example depicted in FIG. 4, the BW driver 312 operates the BW LEDs 304b at a sufficient brightness and intensity so as to support the desired benefit of the BW light output by the BW LEDs 304b. The output of the BW light is regulated by the array of shutters 316 coupled to the controller 314. The shutters 316 open upon receiving a corresponding opening signal from the controller 314, thereby allowing the BW light generated at the BW section 318 to pass through the output of the lighting device 300. Shutters may be controlled together in groups, or each individual one of the shutters may be separately controlled. The shutters 316 close upon receiving a corresponding closing signal(s) from the controller 314, thereby preventing the BW light from passing through the output of the lighting device 300. The controller 314 may be configured to signal a portion of the array of shutters 316 to open and/or close, which can reduce or increase the brightness and intensity of the BW light that passes through the output of the lighting device 300. In such examples, a number shutters in the array of shutters 316 will be open (e.g., open shutter 318a) and a number of shutters will be closed (e.g., closed shutter 318b).

The lighting device 300 may also include an array of similar shutters (not shown) positioned between the GI LEDs 304a and the output of the lighting device 300 that are coupled to the controller to selectively permit GI light to pass through the output. In such examples, the shutters positioned over the GI light section 306 may be controlled independently from the shutters 316 over the BW light section 308. Although not depicted, the controller 314 may be coupled to the BW driver 312 to control the brightness and intensity of the BW LEDs 304b.

It is contemplated that the lighting devices 200 and 300 (and other lighting devices disclosed herein) may incorporate a combination of dimming mechanisms as described relative to FIG. 3 along with any number or arrangement of shutters, such as shutters 316 of FIG. 4, to generate light for general illumination and to generate BW light to support a benefit other than general illumination.

Additionally, more than one beneficial wavelength may be generated by the lighting systems. For example, the arrays 202, 302 of LEDs can be partitioned into a GI light section and multiple BW light sections, with each BW light section having an independent BW driver being capable of generating distinct BWs. Thus, the lighting devices disclosed may include a GI light source, a first BW light source for generating light of a first particular wavelength to support a first intended benefit, a second BW light source for generating light of a second particular wavelength to support a second intended benefit, and so on.

The examples of FIGS. 3 and 4 show the LEDs of the different types in different sections of the arrays. It should be apparent that other arrangements of the LEDs in and about each array may be used. For example, the LEDs for GI output may be dispersed at various locations about the array and the LEDs for BW output may be dispersed about the array so as to be intermingled with the LEDs for GI output.

FIG. 5 illustrates a further example of a lighting device for generating GI light and BW light with a GI light source and a BW light source integrated into the same device. The lighting system 400 includes an array 402 of lights 404 (e.g., LEDs), a polarizer 406 positioned over the lights 404, and a pixelated screen 408. The array 402 of lights 404 may operate as a light source (e.g., a back light) for projecting light toward the pixelated screen 408. The pixelated screen 408 may be a pixelated phosphorescent screen, a pixelated florescent screen, a screen implementing LEDs, phosphors, quantum dots, etc. In the example of FIG. 5, the GI light source (not finely delineated) may be a partitioned section of pixels in the screen 408 that includes pixels dedicated to generating and outputting light for general illumination or may be pixels for general illumination output at selected locations dispersed across the screen area. Additionally, the BW light source (not finely delineated) may be pixels in another partitioned section of the screen 408 or may be pixels at other selected locations dispersed across the screen area, configured to generate and output light of a particular wavelength that supports an intended benefit other than general illumination. Between the polarizer 406 and the screen 408 is an array of LCDs 410. A driver 412 is coupled to the array 402, and a controller 414 is coupled to the driver 412 and the LCDs 410. The LCDs 410 act as shutters and the device may include an LCD shutter corresponding to each pixel on the screen 408. The LCDs 410 can be configured to operate as discrete shutters (e.g., shutters with only an open and closed position), or as gray-scale shutters. The drivers and controller may be implemented in a manner similar to the drivers and controllers in the earlier examples. For convenience, the optical elements coupled to the sources so as to supply both types of light to the device output are not shown specifically in this drawing.

The pixelated screen 408 may include fluorescent materials, such as of any suitable type phosphor, e.g., traditional phosphors, doped semiconductor nanophosphors or quantum dots. Wavelength converting materials absorb excitation energy then re-emit the energy as radiation of a different wavelength than the initial excitation energy. For example, some phosphors produce a down-conversion referred to as a "Stoke shift," in which the emitted radiation has less quantum energy and thus a longer wavelength. Other phosphors produce an up-conversion or "Anti-Stokes shift," in which the emitted radiation has greater quantum energy and thus a shorter wavelength.

Semiconductor nanophosphors, sometimes referred to as Quantum dots (QDs), provide similar shifts in wavelengths of light. QDs are nano scale semiconductor particles, typically crystalline in nature, which absorb light of one wavelength and re-emit light at a different wavelength, much like conventional phosphors. However, unlike conventional phosphors, optical properties of the quantum dots can be more easily tailored, for example, as a function of the size of the dots. In this way, for example, it is possible to adjust the absorption spectrum and/or the emission spectrum of the QDs by controlling crystal formation during the manufacturing process so as to change the size of the QDs. Thus, QDs of the same material, but with different sizes, can absorb and/or emit light of different colors. For at least some exemplary QD materials, the larger the dots, the redder the spectrum of re-emitted light; whereas smaller dots produce a bluer spectrum of re-emitted light.

Doped semiconductor nanophosphors are somewhat similar in that they are nanocrystals formed of semiconductor materials. However, this later type of semiconductor nanophosphors is doped, for example, with a transition metal or a rare earth metal. For white GI light emission, mixtures may use two, three or more doped semiconductor nanophosphors and may further include one or more non-doped semiconductor nanophosphor.

Doped semiconductor nanophosphors may be used individually to generate BW emissions. Doped semiconductor nanophosphors exhibit a relatively large Stokes shift, from shorter wavelength of absorption spectra to longer wavelength emissions spectra. If desirable for a device supporting a number of different BW applications, several doped semiconductor nanophosphor types may be used that are excited in response to a particular electromagnetic energy range but where each type re-emits visible light of a different spectral characteristic. At least for the doped semiconductor nanophosphors, each phosphor emission spectra may then have little or no overlap with excitation or absorption ranges of the doped semiconductor nanophosphors dispersed in the material, so as to support spectrally separate BW emissions without substantial cross-excitation.

Utilizing the properties of the luminescent phosphor materials, each pixel in the screen 408 can be tailored to produce a particular wavelength or range of wavelengths in the spectrum. The phosphors may have different excitation spectra, and use of different phosphors might require use of LEDs emitting multiple types/colors of light to drive the phosphors. In our example, however, we will assume that all of the phosphors used in the various pixels of the screen 408 are of types having emission spectra that overlap each other in a spectral region that includes the emission spectra of a particular type of LED. For example, the screen 408 may use nanophosphors of various types excited in response to near ultraviolet (UV) electromagnetic energy in the range of 380-420 nm and/or of various types excited in response to UV energy in a range of 380 nm and shorter. In such an example, the LEDs 402 therefore all may be of that same particular type, e.g. of a type for emission at a nominal wavelength in the range of 380-420 nm or of a type for emission at a nominal wavelength in the range of 380 nm and shorter.

When light from the LED array 402 is emitted through the polarizer 406, the controller 414 operates the LCD shutters 410 (either discrete or gray-scale) to selectively permit the light to pass and enter the pixels of the screen 408. The pixels, made up of phosphors or quantum dots, will output light of a wavelength corresponding to the properties of each pixel, when the respective LCD pixels of the array 410 allow light to pass through to the phosphor pixels of screen 408 to excite emissions of BWs by those phosphor pixels.

With this structure, sections of the screen 408 can be partitioned such that a section includes only pixels that output a particular wavelength to support a desired benefit (e.g., a BW). Other sections of the screen 408 (or the rest of the screen 408) may include phosphor materials that output various wavelengths which can be combined to produce light for general illumination. Thus, the lighting device 400 can utilize the LCDs 410 to prevent light generated by the array 402 from entering the sections of the screen 408 constructed for outputting the BWs, and to allow light generated by the array 402 to enter the sections of the screen 408 for outputting GI light. The LCDs 410 can be controlled to output both GI light and BWs and either GI light or BWs independent of each other.

In an additional example, the LCDs 410 may be gray-scale shutters, such that various brightness and intensities of the light from the array 402 are permitted to pass through each of the pixels in the screen 408. Controlling an LCD in the LCD array 410 toward the darker end of the gray-scale via the controller 414 sends dimmer, lower intensity light to the phosphor pixel, thus making the subsequent light emitted from the pixel of a lower intensity. Controlling an LCD in the LCD array 410 toward the lighter end of the gray-scale via the controller 414 sends brighter, higher intensity light to the phosphor pixel, making the subsequent light outputted from the pixel of a higher intensity. Utilizing a gray-scale LCD array, the intensity of a section of the screen 408 can be increased such that, if the section is composed of pixels constructed to generate BWs, the intensity of the BW can be set to the sufficient level so as to support the intended benefit of the BW. Similarly, GT light can be controlled to allow user selected dimming.

In addition to the LCD array 410 used in combination with the screen 408, the driver 412 may operate as a dimming mechanism to brighten or dim the lighting array 402, allowing further control of the intensity of both the GI light and the BW light. Some or all of the components of the lighting devices 200, 300, 400, such as dimming mechanisms, shutters, LCD arrays, and pixelated screens, can be combined into a lighting device for generating light for general illumination of a space and generating light of a particular wavelength at a sufficient intensity and duration to support an intended benefit other than general illumination of the space. The lighting devices disclosed herein integrate both a GI light source and a BW light source into a single lighting device, and are constructed such that the intended benefit of the BW light can be supported through control of the intensity, duration, and/or characteristics of the BW light.

Other lighting device arrangements permitting selective excitation of different types of fluorescent materials may be used to generate both GI lighting and BW lighting from one integrated lighting device. A few examples of such other arrangements may be found in U.S. Pat. No. 8,330,373, the full patent disclosure of which is incorporated entirely herein by reference.

The lighting systems disclosed may also be configured to produce a flashing pattern with the BW light to support additional benefits other than general illumination of a space. For example, emitting light of infrared wavelengths at a particular frequency (e.g., at a frequency other than that of the GI light) over a body part of a human produces a therapeutic benefit similar to acupuncture. Flashing patterns of BW light can also be used for medical diagnosis purposes. As an example, flashing BW light over a body part of a human while simultaneously providing GI light for the space can enhance the visual appearance of skin disorders or veins, aiding medical professionals with diagnosis and treatment. Passive objects in the space can also be caused to flash based on the optical characteristics of the objects. The above described benefits that can be supported by outputting patterns of BW light at particular frequencies are exemplary and not exclusive, as it will be understood that the disclosed lighting devices are capable of achieving various benefits by flashing various wavelengths of BW light while producing GI light for general illumination of a space.

Referring back to FIGS. 1-4, the microcontroller 22, the microcontroller 129, the controllers 214 and 314, BW drivers 212 and 312, and/or GI drivers 208 and 310 may be configured to produce the above described flashing patterns. Microcontroller 22 can be programmed to power drivers 21a and/or 21b to alternate between power ON and OFF states so as to produce a flashing pattern. Similarly, microcontroller 129 can be programmed to power the drivers 121, 123, 125, and/or 127 to alternate between power ON and OFF states so as to produce a flashing pattern. Additionally, since the lighting device 200 is capable of producing particular wavelengths of BW light at sufficient intensities and for sufficient durations to support the aforementioned benefits utilizing dimming mechanisms, the BW drivers 212 can configured cycle through periodic intensity changes to regulate a frequency at which the BW light is dimmed, thereby producing flashing patterns of outputted BW light. Similarly, the shutters 316a and 316b of lighting device 300 can be configured to open and close at particular frequencies to produce flashing patterns of BW light. As an example, lighting systems 200 and 300 can be configured to produce flashing patterns to support the acupuncture benefit in lighting fixtures such as desk lamps, table lamps, ceiling fixtures, etc.

Flashing patterns can also be produced with the lighting systems described with respect to FIG. 5. Different combinations of wavelengths produced by the fluorescent phosphor materials in the screen 408 can be used to produce the same color point, such as the color point desired for general illumination of the space. The screen 408 can be manufactured such that the screen 408 includes a pixel for each wavelength in the spectrum. As such, the LCDs 410 may be controlled via the controller 414 to either slowly or rapidly change the combination of wavelengths used for general illumination while keeping the color point of the general illumination light the same. By changing, back and forth over a period of time, the combination of wavelengths (e.g., the spectra) while keeping the color point of the general illumination the same, passive objects in the space with optical characteristics responsive to the changing spectra will flash while the space remains under general illumination. Thus, the BW generated is the wavelength at which the passive object in the room flashes under such changes. The slow or rapid change causes the BW to change in intensity, and the object(s) responsive to the changing intensity of the BW appear to flash as the intensity changes.

This flashing pattern may be done with any wavelength of light that can be produced by the fluorescent phosphor materials. For example, signs may be placed in the space that flash when exposed to ultraviolet light, or other objects such as ink pens will flash in response to changing intensities of particular wavelengths of visible light. Another example includes a lighting system with multiple modes designed for sanitation in a space that includes a warning sign that flashes upon exposure to ultraviolet light. In a first mode, the lighting system produces GI light for general illumination of the space. In a second "warning" mode, the lighting system changes the spectra to generate a flashing lower intensity ultraviolet BW light while keeping the color point for general illumination the same, causing the warning sign to flash and indicating that the sanitation mode is about to begin. In a third mode, the lighting system no longer alters the intensity of the BW light so support the flashing effect of the sign, and now increases the intensity of the ultraviolet BW light to support the sanitation benefit. In the third mode, the GI light can still be generated by the lighting system. Thus, it is contemplated that multiple intended benefits (e.g., object flashing and sanitation with the same beneficial wavelength at different intensities, durations, and characteristics) can be supported through independent intensity, duration, and characteristic control of BWs in lighting devices constructed for both general illumination of a space and supporting intended benefits other than general illumination with BWs.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A lighting device, comprising:
   a first light source;
   a second light source;
   a third light source;
   the first light source configured to generate light for illumination of a room;
   the second light source configured to generate light of a first particular wavelength independently from the first light source,
   the third light source configured to generate light of a second particular wavelength independently from the first light source and the second light source, the second particular wavelength of the third light source being different from the first particular wavelength of the second light source, wherein:

the light generated by the second light source is output at an intensity that supports a first benefit provided the light output by the second light source other than illumination of the space, the light generated by the third light source is output at an intensity that supports a second benefit provided by the light output by the third light source other than illumination of the room, the second benefit is different from the first benefit, the first, the second and the third light sources are integrated into the lighting device; and an optical processing element, the optical processing element being coupled to the first, second and third light sources, configured to produce a combined light output of the lighting device into the room, the combined light output including:
  i) the light for illumination of the room from the first light source, and
  ii) the light of the first particular wavelength from the second light source, and
  iii) the light of the second particular wavelength from the third light source via the light output of the lighting device.

2. The lighting device of claim 1, further comprising a microcontroller providing control of the second and third light sources independent from the first light source.

3. The lighting device of claim 1, wherein the first particular wavelength output by the second light source is a wavelength reasonably expected to support a therapeutic benefit for a human or other biological entity as the first benefit.

4. The lighting device of claim 3, further comprising a driver circuit configured to output the light of the first particular wavelength in a pattern of a predetermined frequency other than a frequency of the outputted general illumination light.

5. The lighting device of claim 4, wherein the first particular wavelength output by the second light source is a wavelength that supports an acupuncture-like effect as the first benefit.

6. The lighting device of claim 5, wherein the first particular wavelength is an infrared wavelength.

7. The lighting device of claim 3, wherein the first particular wavelength output by the second light source is a wavelength that supports stimulation or suppression in an exposed organism of at least one of a group consisting of: vitamin growth, hormone production, plant growth, and wound healing, as the first benefit.

8. The lighting device of claim 3, wherein the first particular wavelength output by the second light source is a wavelength that supports Mastocytosis treatment as the first benefit.

9. The lighting device of claim 8, wherein the first particular wavelength is about 540 nanometers.

10. The lighting device of claim 1, wherein the first particular wavelength output by the second light source is a wavelength that supports at least one of a group consisting of: blood illumination, dust illumination, ultraviolet sanitation, and diagnosis of a medical condition, as the first benefit.

11. The lighting device of claim 1, further comprising a microcontroller to operate the first, second, and third light sources to output the light for illumination of the space, light for the first benefit and the light for the second benefit simultaneously via the light output of the lighting device.

12. A lighting device, comprising:
a first light source and a second light source, the first light source configured to generate light for illumination of a space;
the second light source configured to generate light of a particular wavelength independently from the first light source, wherein;
the light generated by the second light source is output at a sufficient intensity to support a benefit other than illumination of the space, and
the first and second light source are integrated into the lighting device;
an optical processing element, configured to produce a light output of the lighting device, coupled to the first and second light sources, so as to output the light for illumination of the space from the first light source and the light of the particular wavelength for the other benefit from the second light source via the light output of the lighting device;
at least one shutter; and
a controller coupled to the at least one shutter, the controller being configured to selectively permit light generated from the second light source to be output through the at least one shutter.

13. The lighting device of claim 12, wherein the at least one shutter is a liquid crystal shutter, a mechanical shutter, or a microelectromechanical shutter.

14. A method of lighting a room, comprising:
generating, from a general illumination light source integrated into a lighting device, light for illumination of the room;
generating, from a first beneficial wavelength light source integrated into the lighting device, light of a first particular wavelength independently from the generating of light for illumination of the room;
generating, from a second beneficial wavelength light source integrated into the lighting device, light of a second particular wavelength independently from the generating of light for illumination of the room and independent from the first beneficial wavelength light source;
combining the generated light of the first and second particular wavelengths and the generated light from the general illumination light source for general illumination; and
outputting, via a light output of the lighting device, the combined light, wherein the light of the first and second particular wavelengths generated from the first and second beneficial wavelength light sources is output at a sufficient intensity and duration to support at least a benefit other than illumination of the room.

15. The method of claim 14, wherein the step of generating light of the first particular wavelength comprises:
increasing a brightness of the first beneficial wavelength light source independently from the general illumination light source.

16. A method comprising:
generating, from a general illumination light source integrated into a lighting device, light for illumination of a space;
generating, from a beneficial wavelength light source integrated into the lighting device, light of a particular wavelength independently from the generating of light for illumination of the space by changing, with a pixelated screen and an LCD shutter array, a wavelength combination used to generate the light for illumination while maintaining a color point of the light for illumination;

combining the generated light of the particular wavelength and the generated light for illumination; and outputting, via a light output of the lighting device, the combined light, wherein the light of the particular wavelength generated from the beneficial wavelength light source is output at a sufficient intensity and duration to support a benefit other than illumination of the space.

17. A lighting device, comprising:

a pixelated screen configured to output light for general illumination of a space and a particular wavelength that provides a therapeutic benefit;

a light source configured to project light toward the pixelated screen;

a first set of pixels in the pixelated screen adapted to generate and output light for general illumination of the space upon receiving the projected light from the light source; and a second section of pixels in the pixelated screen adapted to generate and output light of a particular wavelength independently from the first set of pixels upon receiving the projected light from the light source, wherein the light of the particular wavelength is outputted at a sufficient intensity that supports the provided therapeutic benefit other than general illumination of the space.

18. The lighting device of claim 17, further comprising an array of shutters positioned between the light source and the pixelated screen configured to selectively permit the projected light to pass to the pixelated screen.

19. The lighting device of claim 18, wherein the array of shutters comprises gray-scale LCD shutters.

20. The lighting device of claim 17, wherein the pixelated screen comprises quantum dot pixels.

* * * * *